United States Patent
Baranowitz

(10) Patent No.: US 12,352,535 B2
(45) Date of Patent: Jul. 8, 2025

(54) IMPACT RESISTANT MATERIAL

(71) Applicant: Steven Baranowitz, Wyncote, PA (US)

(72) Inventor: Steven Baranowitz, Wyncote, PA (US)

( * ) Notice: Subject to any disclaimer, the term of this patent is extended or adjusted under 35 U.S.C. 154(b) by 836 days.

(21) Appl. No.: 17/253,390

(22) PCT Filed: Jun. 17, 2019

(86) PCT No.: PCT/US2019/037423
§ 371 (c)(1),
(2) Date: Dec. 17, 2020

(87) PCT Pub. No.: WO2019/245941
PCT Pub. Date: Dec. 26, 2019

(65) Prior Publication Data
US 2021/0269450 A1    Sep. 2, 2021

Related U.S. Application Data

(60) Provisional application No. 62/687,852, filed on Jun. 21, 2018.

(51) Int. Cl.
| | |
|---|---|
| *F41H 1/02* | (2006.01) |
| *A61K 31/407* | (2006.01) |
| *B29C 70/46* | (2006.01) |
| *C07D 487/06* | (2006.01) |
| *C08K 5/3417* | (2006.01) |
| *C08L 65/02* | (2006.01) |
| *F41H 5/04* | (2006.01) |

(52) U.S. Cl.
CPC .......... *F41H 1/02* (2013.01); *A61K 31/407* (2013.01); *C07D 487/06* (2013.01); *C08K 5/3417* (2013.01); *C08L 65/02* (2013.01); *F41H 5/0421* (2013.01); *F41H 5/0428* (2013.01); *B29C 70/46* (2013.01); *B29K 2065/00* (2013.01)

(58) Field of Classification Search
None
See application file for complete search history.

(56) References Cited

U.S. PATENT DOCUMENTS

| | | | | |
|---|---|---|---|---|
| 5,036,115 A | * | 7/1991 | Gallas | G02C 7/04 |
| | | | | 252/588 |
| 5,047,447 A | * | 9/1991 | Gallas | G02C 7/108 |
| | | | | 252/588 |
| 5,112,883 A | * | 5/1992 | Gallas | G02B 1/105 |
| | | | | 252/588 |
| 5,538,752 A | * | 7/1996 | Blanchette | A01N 63/10 |
| | | | | 252/384 |
| 6,034,003 A | * | 3/2000 | Lee | D06P 1/65112 |
| | | | | 442/131 |
| 6,103,777 A | * | 8/2000 | Krishnan | G02B 1/041 |
| | | | | 523/105 |
| 7,029,758 B2 | * | 4/2006 | Gallas | B32B 27/08 |
| | | | | 264/1.32 |
| 8,586,090 B2 | * | 11/2013 | Dadachova | A61K 31/405 |
| | | | | 600/1 |
| 2003/0092794 A1 | * | 5/2003 | Gallas | B32B 27/08 |
| | | | | 523/137 |
| 2004/0145802 A1 | * | 7/2004 | Miniutti | G02C 7/02 |
| | | | | 351/159.62 |
| 2007/0237829 A1 | * | 10/2007 | Dadachova | A61K 9/0019 |
| | | | | 977/774 |
| 2009/0323179 A1 | * | 12/2009 | Kawai | B32B 27/40 |
| | | | | 252/589 |
| 2020/0024797 A1 | * | 1/2020 | Wang | C12P 17/10 |

FOREIGN PATENT DOCUMENTS

| | | | | | |
|---|---|---|---|---|---|
| CN | 102604293 A | * | 7/2012 | ......... | B29C 47/0011 |
| CN | 106866918 A | | 6/2017 | | |
| CN | 107298838 A | * | 10/2017 | ............ | C08K 5/00 |
| ES | 2562330 T3 | * | 3/2016 | ............ | B27D 1/08 |
| WO | WO-2018009032 A1 | * | 1/2018 | ............ | B29C 71/02 |

OTHER PUBLICATIONS

Machine Translation CN102604293 (Year: 2012).*
Machine Translation CN107298838 (Year: 2017).*
Machine Translation ES2562330 (Year: 2016).*
Machine Translation WO2018009032 (Year: 2018).*
International Preliminary report dated Dec. 30, 2020.
Wang, Y., et al Superior Performance of Polyurethane Based on Natural Melanin Nanoparticles, Biomacromolecules 2016, vol. 17, pp. 3782-3789.
Wang, Y., et al Strong nanocomposite reinforcement effects in poly(vinyl alcohol) with melanin nanoparticles, RSC Adv., 2015, 5, 72691-72698.
International Preliminary Report on Patentability for International Application No. PCT/US2019/037423 dated Dec. 22, 2020.
Office Action for Israeli Patent Application No. 279600 issued on Dec. 10, 2023.
Second Examination Report for Indian Patent Application No. 202027053563 issued on Nov. 8, 2023.

(Continued)

*Primary Examiner* — Jennifer A Steele

(74) *Attorney, Agent, or Firm* — Potomac Law Group, PLLC; Joseph F. Murphy

(57) ABSTRACT

The current disclosure is directed to an impact resistant material made from a novel melanin composite. It has been found that using these composites allows for the production of effective ballistic protection and blast containment materials.

6 Claims, No Drawings

(56) References Cited

OTHER PUBLICATIONS

Office Action for Australian Application No. 2019289148 issued on Mar. 26, 2024.
Office Action for Korean Patent Application No. 10-2020-7038133 issued on Apr. 29, 2024 (includes English language translation).
Notice of Acceptance for Australian Patent Application No. 2019289148 mailed on Jan. 17, 2025.
Office Action for Australian Patent Application No. 2019289148 issued on Jan. 2, 2025.

* cited by examiner

1

IMPACT RESISTANT MATERIAL

CROSS-REFERENCE TO RELATED APPLICATIONS

This application is a U.S. National Phase Application of PCT/2019/037423, filed Jun. 17, 2019, which claims priority to U.S. Application Ser. No. 62/687,852, filed Jun. 21, 2018, the contents of which applications are incorporated herein by reference in their entireties for all purposes.

BACKGROUND OF THE INVENTION

The current disclosure is directed to a ballistic protection material made from a novel melanin polymer composite. It has been found that using these composites allows for the production of effective ballistic protection and blast containment materials.

Military personnel want lightweight, fast and maneuverable vehicles, but they also want vehicle occupants to be fully protected. Ballistic steel armor plates, while relatively inexpensive, add thousands of pounds to a vehicle, many of which were not designed to carry such loads. This has resulted in numerous engine and transmission failures as well as problems with vehicle suspensions and brakes. The additional weight reduces fuel efficiency and makes it impossible to carry additional personnel in the vehicle in case of emergency. For these reasons, designers are beginning to adopt more lightweight composite armor across the board for military and tactical vehicles.

The present disclosure relates generally to composites of melanin materials and non-melanin materials such as ceramics, fibrous sheets and/or laminated plies. The inventor has appreciated that by combining certain melanin materials and non-melanin materials into ceramics, laminar configurations, and composites with advantages not attainable by either component separately can be achieved. In some cases, the resulting composite, synergistic interactions between the fibrous materials and melanin materials may arise.

Melanin composites may take many forms and have many different useful advantages. Melanin composites comprising mechanically strong melanin materials are particularly useful. In some embodiments, melanin composites are particularly well-suited as multilayer insulation (MLI) with better thermal performance than the melanin material by itself. In some embodiments, melanin composites with good flexibility may serve as useful insulation for garments. In other embodiments, melanin composites are highly effective ballistic materials useful for bullet-proof vests, armored vehicle cladding, and energetic flames or jets. In some embodiments, melanin composites may be useful in space applications including micrometeoroid/space debris protection and vehicle reentry shielding. In further embodiments, melanin composites may serve as high stiffness-to-weight ratio materials suitable for lightweight structures, aircraft and automotive parts, and high-performance sports equipment.

The melanin composite exhibits the following features: 1. Ultra-light-weight; 2. Flexibility to fit various vehicle bodies and contours; 3. Superior impact energy absorption capability; 4. Superior strength for structural integrity; 5. Capability to resist heat and flame; 6. Ease of manufacture, maintenance and repair, and low life-cycle cost; 7. Applicability to other military applications and to commercial vehicle systems.

Due to the flexibility of the proposed system, the new melanin composite material can also be used, with minimum modifications, to protect commercial vehicles when necessary. The melanin composite can be further extended for other usages, for example, in a chair-based melanin composite to protect driver and passengers, or attached to office walls to protect officers, or even as a personal armor.

In addition, the disclosure provides a pharmaceutical composition comprising: at least one melanin material; optionally, at least one additional pharmaceutically active agent; optionally, at least one additional pharmaceutically acceptable carrier, wherein the pharmaceutical composition is formulated or manufactured as a liquid, an elixir, an aerosol, a spray, a powder, a tablet, a pill, a capsule, a gel, a geltab, a nano-suspension, a nano-particle, an extended release dosage form, or a topical formulation, further wherein the pharmaceutical composition is a therapeutically effective for treating a condition in a patient.

The melanins comprise a family of biopolymer pigments. Progress understanding the structure, functions, chemical and physical properties of melanins has been slow, sporadic and fragmented among many different scientific disciplines, including biology, chemistry, physics, and electronics.

There are a number of different schemes for classifying melanin. These include the following:
By color: e.g., most known melanins have been black, brown, or red, although other colors have been produced synthetically,
Natural versus synthetic,
By category: Eumelanin, phaeomelanin, neuromelanin, allomelanin,
By source: animal, plant, fungal, lichen, etc.,
By suitability to different extraction methods,
By chemical structure,
By physical properties, and
By biological functions.

The definition and nomenclature of melanin remains unsettled and problematic, since workers in various scientific disciplines differ somewhat in their use of the term. For instance, chemists can produce different synthetic melanins using different pathways, but vary in how they characterize the resulting substances. Also, biologists sometimes struggle with the exact definition of melanin, since many melanins extracted from different organisms have similar chemical and physical properties, but remain largely insoluble in most common solvents, and resist many types of chemical and physical analysis.

A frequently used chemical description of melanin is that it is comprised of "heteropolymers of 5-6-dihydroxyindole and 5-6-dihydroxyindole-2-carboxylic acid" (Bettinger et al., 2009).

Accordingly, it would be desirable to have lightweight melanin composite ballistic protection materials that are easy to fabricate into final armor components, at reasonable cost, yet still offer ballistic protection properties on par with heavier armor materials. Such materials would find ready use in a number of applications, including personal armor (military, law enforcement, civilian); vehicle armor (especially cars and light transport vehicles); aircraft armor (especially rotary wing aircraft); blast containment (e.g., shipping containers) and other applications that are weight sensitive.

All references cited herein are incorporated herein by reference in their entireties.

BRIEF SUMMARY

The disclosure provides a ballistic protection material formed using a composition comprising: melanin material; optionally, at least one additional non-melanin material selected from the group consisting of biological material, biological polymers, polymers, metals, radionuclides, iron, copper, zinc, cesium, radium, strontium, thorium, uranium, salts, ceramics, clothing, construction materials, existing armor materials, poly-paraphenylene terephthalamide, and other natural materials or their synthetic mimics. The disclosure provides a ballistic protection material wherein the ballistic protection material is manufactured in a form selected from the group consisting of particles, nanoparticles, dust, beads, fibers that are woven, fibers that are non-woven, sheets, films, slabs, plates, bricks, chars, spheres, nodules, balls, graphite-like sheets and shards, liquids, gels, solids, thermoplastic solids, and thermoset solids. The disclosure provides a ballistic protection material wherein the non-melanin material is collagen. The disclosure provides a ballistic protection material wherein the non-melanin material is selected from the group consisting of a polyphenylene polymer, polyimides, polyetherimides, polyimideamides, polysulfones, epoxy resins, bismaleimide resins, bis-benzocyclobutene resins, phthalonitrile resins, polyaryletherketones, polyetherketones, liquid crystal polymers, oligomeric cyclic polyester precursors, polybenzbisoxazoles, polybenzbisthiazoles, polybenzbisimidazoles, acetylene endcapped thermosetting resins, polysulfones, polyaramides, Poly-paraphenylene terephthalamide, polyamides, polycarbonates, polyethylenes, polyesters, and combinations thereof. The disclosure provides a ballistic protection material wherein the non-melanin material is a ceramic material selected from the group consisting of alumina, boron carbide, boron nitride, mullite, silica, silicon carbide, silicon nitride, magnesium boride, multi-walled carbon nanotubes, single walled carbon nanotubes, group IVB, VB and VIB metal sulfide nanotubes, titanium boride, titanium carbide, diamond, and combinations thereof. The disclosure provides a ballistic protection material wherein the non-melanin material and the melanin material are present in a ratio selected from the group consisting of about 2 to about 98, about 5 to about 95, about 20 to about 80, about 30 to about 70, about 40 to about 60, about 50 to about 50, about 60 to about 40 about 70 to about 30 about 80 to about 20, about 95 to about 5, about 98 to about 2 (percent by weight). The disclosure provides a ballistic protection material wherein the non-melanin material and the melanin material combine to synergistically increase the impact resistance of the ballistic protection material compared to the non-melanin materials and melanin material alone. The disclosure provides a ballistic protection material wherein the ballistic protection material is formed into an article which is an item selected from the group consisting of helmets, body armor, vehicle armor, aircraft armor, watercraft armor, structure armor, equipment housing, blast protection panels, ballistic protection panels, and cargo containers.

The disclosure provides a process for forming a ballistic protection material comprising: mixing a melanin material; and optionally, at least one additional non-melanin material selected from the group consisting of polymers, metals, radionuclides, iron, copper, zinc, cesium, radium, strontium, thorium, uranium, salts, ceramics, clothing, construction materials, existing armor materials, Poly-paraphenylene terephthalamide, other natural materials or their synthetic mimics; and shaping the resultant material into an article. The disclosure provides a process wherein the ballistic protection material is manufactured in a form selected from the group consisting of particles, nanoparticles, dust, beads, fibers that are woven, fibers that are non-woven, sheets, films, plates, bricks, chars, spheres, nodules, balls, graphite-like sheets and shards, liquids, gels, solids, thermoplastic solids, and thermoset solids. The disclosure provides a process wherein the step of shaping comprises using a technique selected from the group consisting of molding, compression molding, stamping, bending, thermoforming, injection molding, additive manufacturing, coining, and extruding. The disclosure provides a process wherein the melanin material and the non-melanin material are mixed using a machine selected from the group consisting of a single screw extruder, a counter-rotating twin-screw extruder, a co-rotating twin-screw extruder, a Henschel mixer, and a co-kneader. The disclosure provides a process wherein the non-melanin material is selected from the group consisting of a polyphenylene polymer, polyimides, polyetherimides, polyimideamides, polysulfones, epoxy resins, bismaleimide resins, bis-benzocyclobutene resins, phthalonitrile resins, polyaryletherketones, polyetherketones, liquid crystal polymers, oligomeric cyclic polyester precursors, polybenzbisoxazoles, polybenzbisthiazoles, polybenzbisimidazoles, acetylene endcapped thermosetting resins, polysulfones, polyaramides, Poly-paraphenylene terephthalamide, polyamides, polycarbonates, polyethylenes, polyesters, and combinations thereof. The disclosure provides a process wherein the non-melanin material is a ceramic material selected from the group consisting of alumina, boron carbide, boron nitride, mullite, silica, silicon carbide, silicon nitride, magnesium boride, multi-walled carbon nanotubes, single walled carbon nanotubes, group IVB, VB and VIB metal sulfide nanotubes, titanium boride, titanium carbide, diamond, and combinations thereof. The disclosure provides a process wherein the ballistic protection material is formed into an article which is an item selected from the group consisting of helmets, body armor, vehicle armor, aircraft armor, watercraft armor, structure armor, equipment housing, blast protection panels, ballistic protection panels, and cargo containers.

The disclosure provides a composite material comprising: melanin material; optionally, at least one additional non-melanin material selected from the group consisting of polymers, metals, radionuclides, iron, copper, zinc, cesium, radium, strontium, thorium, uranium, salts, ceramics, clothing, construction materials, existing armor materials, Poly-paraphenylene terephthalamide, and other natural materials or their synthetic mimics. The disclosure provides a composite material wherein the non-melanin material is manufactured as in a from selected from the group consisting of particles, nanoparticles, dust, beads, fibers that are woven, fibers that are non-woven, sheets, films, plates, bricks, chars, spheres, nodules, balls, graphite-like sheets and shards, liquids, gels, solids, thermoplastic solids, and thermoset solids. The disclosure provides a composite material wherein the additional non-melanin material is selected from the group consisting of a polyphenylene polymer, polyimides, polyetherimides, polyimideamides, polysulfones, epoxy resins, bismaleimide resins, bis-benzocyclobutene resins, phthalonitrile resins, polyaryletherketones, polyetherketones, liquid crystal polymers, oligomeric cyclic polyester precursors, polybenzbisoxazoles, polybenzbisthiazoles, polybenzbisimidazoles, acetylene endcapped thermosetting resins, polysulfones, polyaramides, Poly-paraphenylene terephthalamide, polyamides, polycarbonates, polyethylenes, polyesters, and combinations thereof. The disclosure provides a composite material wherein the non-melanin material is a ceramic material selected from the group consisting of alumina, boron carbide, boron nitride, mullite, silica, silicon carbide, silicon nitride, magnesium boride, multi-walled carbon nanotubes, single walled carbon nanotubes, group IVB, VB and VIB metal sulfide nanotubes, titanium boride, titanium carbide, diamond, and combinations thereof. The disclosure provides a composite material wherein the non-melanin material and the melanin material are present in a ratio selected from the group consisting of about 2 to about 98, about 5 to about 95, about 20 to about 80, about 30 to about 70, about 40 to about 60, about 50 to about 50, about 60 to about 40 about 70 to about 30 about 80 to about 20, about 95 to about 5, about 98 to about 2 (percent by weight). The disclosure provides a composite material wherein the non-melanin material and the melanin material combine to synergistically increase the impact resistance of the ballistic protection material compared to the non-melanin materials and melanin material alone. The disclosure provides a composite material wherein the material is formed into an article which is an item selected from the group consisting of helmets, body armor, vehicle armor, aircraft armor, watercraft armor, structure armor, equipment housing, blast protection panels, ballistic protection panels, and cargo containers. The disclosure provides a composite material wherein the polymer matrix is formed at least partially of a thermosetting resin. The disclosure provides a composite material wherein the non-melanin is formed at least partially of a thermoplastic. The disclosure provides a composite material wherein the non-melanin is formed at least partially of a polyarylene having one of either a rigid-rod or semi-rigid-rod structure where the structure is formed of a plurality of repeat units where 25% of the repeat units are rigid-rod repeat units having substantially parallel bonds. The disclosure provides a composite material wherein the non-melanin is formed of at least a polyphenylene polymer. The disclosure provides a composite material wherein non-melanin further comprises at least one other polymer independently selected from the group consisting of polyimides, polyetherimides, polyimideamides, polysulfones, epoxy resins, bismaleimide resins, bis-benzocyclobutene resins, phthalonitrile resins, polyaryletherketones, polyetherketones, liquid crystal polymers, oligomeric cyclic polyester precursors, polybenzbisoxazoles, polybenzbisthiazoles, polybenzbisimidazoles, acetylene endcapped thermosetting resins, polysulfones, polyaramides, Poly-paraphenylene terephthalamide, polyamides, polycarbonates, polyethylenes, and polyesters. The disclosure provides a composite material wherein the non-melanin material comprises one or more ceramic powders or particles selected from the group consisting of alumina, boron carbide, boron nitride, mullite, silica, silicon carbide, silicon nitride, magnesium boride, multi-walled carbon nanotubes, single walled carbon nanotubes, group IVB metal sulfide nanotubes, group VB metal sulfide nanotubes, group VIB metal sulfide nanotubes, titanium boride, titanium carbide and diamond. The disclosure provides a composite material further comprising at least one additive material selected from the group consisting of process aids, modifiers, colorants, fibers, adhesion promoters and fillers. The disclosure provides a composite material wherein the material is formed into an article which is an item selected from the group consisting of helmets, body armor, vehicle armor, aircraft armor, watercraft armor, structure armor, equipment housing, blast protection panels, ballistic protection panels and cargo containers.

The disclosure provides a process for forming a composite material comprising: mixing a melanin material; optionally, at least one additional non-melanin material selected from the group consisting of polymers, metals, radionuclides, iron, copper, zinc, cesium, radium, strontium, thorium, uranium, salts, ceramics, clothing, construction materials, existing armor materials, Poly-paraphenylene terephthalamide, other natural materials or their synthetic mimics; and shaping the composite material into an article. The disclosure provides a process wherein the step of shaping comprises using a technique selected from the group consisting of molding, compression molding, stamping, bending, thermoforming, injection molding, additive manufacturing, coining, and extruding. The disclosure provides a process wherein the melanin material and the non-melanin material are mixed using a machine selected from the group consisting of a single screw extruder, a counter-rotating twin-screw extruder, a co-rotating twin-screw extruder, a Henschel mixer, and a co-kneader. The disclosure provides a process wherein the non-melanin material is selected from the group consisting of a polyphenylene polymer, polyimides, polyetherimides, polyimideamides, polysulfones, epoxy resins, bismaleimide resins, bis-benzocyclobutene resins, phthalonitrile resins, polyaryletherketones, polyetherketones, liquid crystal polymers, oligomeric cyclic polyester precursors, polybenzbisoxazoles, polybenzbisthiazoles, polybenzbisimidazoles, acetylene endcapped thermosetting resins, polysulfones, polyaramides, Poly-paraphenylene terephthalamide, polyamides, polycarbonates, polyethylenes, polyesters, and combinations thereof. The disclosure provides a process wherein the non-melanin material is selected from the group consisting of alumina, boron carbide, boron nitride, mullite, silica, silicon carbide, silicon nitride, magnesium boride, multi-walled carbon nanotubes, single walled carbon nanotubes, group IVB, VB and VIB metal sulfide nanotubes, titanium boride, titanium carbide, diamond, and combinations thereof. The disclosure provides a process wherein the non-melanin material and the melanin material are present in a ratio selected from the group consisting of about 2 to about 98, about 5 to about 95, about 20 to about 80, about 30 to about 70, about 40 to about 60, about 50 to about 50, about 60 to about 40 about 70 to about 30 about 80 to about 20, about 95 to about 5, about 98 to about 2 (percent by weight). The disclosure provides a process wherein the non-melanin material and the melanin material combine to synergistically increase the impact resistance of the ballistic protection material compared to the non-melanin materials and melanin material alone. The disclosure provides a process wherein the material is formed into an article which is an item selected from the group consisting of helmets, body armor, vehicle armor, aircraft armor, watercraft armor, structure armor, equipment housing, blast protection panels, ballistic protection panels, and cargo containers.

The disclosure provides a method of preparation of melanin material comprising: providing a melanin source selected from the group consisting of squid ink, cuttlefish ink, octopus ink, natural melanin, synthetic melanin, mushrooms, and combinations thereof; applying microwave radiation, thereby producing a melanin material.

The disclosure provides a method of preparation of melanin material comprising: providing a melanin source selected from the group consisting of squid ink, cuttlefish ink, octopus ink, natural melanin, synthetic melanin, mushrooms, and combinations thereof; applying microwave radiation; applying compression; Thereby producing a melanin material. The disclosure provides a method wherein the compression is applied in a hydraulic press. The disclosure provides a method wherein the hydraulic press ranges in capacity from approximately 1 ton/in$^2$ to 500 tons/in$^2$, 1 ton/in$^2$ to 50 tons/in$^2$, 50 tons/in$^2$ to 100 tons/in$^2$, 1 ton/in$^2$ to 100 tons/in$^2$, 50 tons/in$^2$ to 200 tons/in$^2$, or 1 ton/in$^2$ to 200 tons/in$^2$. The disclosure provides a method wherein the hydraulic press applies compression of approximately 500 tons/in$^2$.

The disclosure provides a pharmaceutical composition comprising: at least one melanin material; optionally, at least one additional pharmaceutically active agent; optionally, at least one additional pharmaceutically acceptable carrier, wherein the pharmaceutical composition is formulated or manufactured as a liquid, an elixir, an aerosol, a spray, a powder, a tablet, a pill, a capsule, a gel, a geltab, a nano-suspension, a nano-particle, an extended release dosage form, or a topical formulation, further wherein the pharmaceutical composition is a therapeutically effective for treating a condition in a patient.

The disclosure provides a process for making a pharmaceutical composition comprising: Providing at least one melanin material; Optionally providing at least one additional pharmaceutically active agent; Optionally providing at least one additional pharmaceutically acceptable carrier, Mixing the at least one melanin material, if present the at least one additional pharmaceutically active agent, and if present the at least one additional pharmaceutically acceptable carrier, thereby forming a pharmaceutical composition, further wherein the pharmaceutical composition is a therapeutically effective for treating a condition in a patient.

The disclosure provides a method of preparation of melanin material comprising: providing a melanin source selected from the group consisting of squid ink, cuttlefish ink, octopus ink, natural melanin, synthetic melanin, mushrooms, and combinations thereof; providing a metal selected from the group consisting of iron, copper, zinc, cesium, radium, strontium, thorium, uranium, and combinations thereof; applying microwave radiation to the melanin source to form a dried melanin source; mixing the metal with the dried melanin source; optionally, applying compression; thereby producing a melanin material. The disclosure provides a method wherein the compression is applied in a hydraulic press. The disclosure provides a method wherein the hydraulic press ranges in capacity from approximately 1 ton/in$^2$ to 500 tons/in$^2$, 1 ton/in$^2$ to 50 tons/in$^2$, 50 tons/in$^2$ to 100 tons/in$^2$, 1 ton/in$^2$ to 100 tons/in$^2$, 50 tons/in$^2$ to 200 tons/in$^2$, or 1 ton/in$^2$ to 200 tons/in$^2$. The disclosure provides a method wherein the hydraulic press applies compression of approximately 500 tons/in$^2$.

DETAILED DESCRIPTION

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to he construed as preferred or advantageous over other embodiments.

In carrying out the method of the present disclosure, the composition of the disclosure may be administered to mammalian species, such as dogs, cats, humans, etc. and as such may be incorporated in a conventional systemic dosage form, such as a tablet, capsule, elixir or injectable. The dosage forms may also include the necessary carrier material, excipient, lubricant, buffer, anti-bacterial, bulking agent, anti-oxidants, or the like.

The terms "treating" and "treatment" used to refer to treatment of a condition in a subject includes: preventing, inhibiting or ameliorating the condition in a subject, such as slowing progression of the condition and/or reducing or ameliorating a sign or symptom of the condition; and preventing, inhibiting or ameliorating a side-effect of a condition in a subject.

"Patient" for the purposes of the present disclosure includes humans and other animals, particularly mammals. Thus the compositions and methods are applicable to both human therapy and veterinary applications. In certain embodiments the subject is a mammal, and in a preferred embodiment the subject is human.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

Melanins

The melanins comprise a family of biopolymer pigments. A frequently used chemical description of melanin is that it is comprised of "heteropolymers of 5-6-dihydroxyindole and 5-6-dihydroxyindole-2-carboxylic acid" (Bettinger et al., 2009). Melanins are polymers produced by polymerization of reactive intermediates. The polymerization mechanisms include, but are not limited to, autoxidation, enzyme-catalyzed polymerization and free radical initiated polymerization. The reactive intermediates are produced chemically, electrochemically, or enzymatically from precursors. Suitable enzymes include, but are not limited to, peroxidases, catalases, polyphenol oxidases, tyrosinases, tyrosine hydroxylases, and laccases. The precursors that are connected to the reactive intermediates are hydroxylated aromatic compounds. Suitable hydroxylated aromatic compounds include, but are not limited to 1) phenols, polyphenols, aminophenols and thiophenols of aromatic or polycyclicaromatic hydrocarbons, including, but not limited to, phenol, tyrosine, pyrogallol, 3-aminotyrosine, thiophenol and α-naphthol; 2) phenols, polyphenols, aminophenols, and thiophenols of aromatic heterocyclic or heteropoly cyclic hydrocarbons such as, but not limited to, 2-hydroxypyrrole, 4-hydroxy-1,2-pyrazole, 4-hydroxypyridine, 8-hydroxyquinoline, and 4,5-dihydroxybenzothiazole.

The term melanin includes naturally occurring melanin polymers as well as melanin analogs as defined below. Naturally occurring melanins include eumelanins, phaeomelanins, neuromelanins and allomelanins.

As used here, the term "melanin" refers to melanins, melanin precursors, melanin analogs, melanin variants, melanin derivatives, and melanin-like pigments, unless the context dictates otherwise. The term "melanin-like" also refers to hydrogels with melanin-like pigmentation and quinoid electrophilicity. This electrophilicity can be exploited for facile coupling with biomolecules.

As used herein, the term "melanin analog" refers to a melanin in which a structural feature that occurs in naturally-occurring or enzymatically-produced melanins is replaced by a substituent divergent from substituents traditionally present in melanin. An example of such a substituent is a selenium, such as selenocysteine, in place of sulfur.

As used herein, the term "melanin derivative" refers to any derivative of melanin which is capable of being converted to either melanin or a substance having melanin activity.

An example of a melanin derivative is melanin attached to a dihydrotrigonelline carrier such as described in Bodor, N., Ann. N.Y. Acad. Sci. 507, 289 (1987), which enables the melanin to cross the blood-brain barrier. The term melanin derivatives is also intended to include chemical derivatives of melanin, such as an esterified melanin.

As used herein, the term "melanin variant" refers to various subsets of melanin substances that occur as families of related materials. Included in these subsets, but not limited thereto, are:

(1) Naturally occurring melanins produced by whole cells that vary in their chemical and physical characteristics;
(2) Enzymatically produced melanins prepared from a variety of precursor substrates under diverse reaction conditions;
(3) Melanin analogs in which a structural feature that occurs in (1) or (2) above is replaced by an unusual substituent divergent from the traditional; and
(4) Melanin derivatives in which a substituent in a melanin produced in (1), (2) or (3) above is further altered by chemical or enzymatic means.

As used herein, the term "Melanin-like substances" refers to heteropolymers of 5-6-dihydroxyindole and 5-6-dihydroxyindole-2-carboxylic acid which have one or more properties usually associated with natural melanins, such as UV absorption or semiconductor behavior.

Melanin Sources

Melanin and Melanin-like compounds can be obtained:
by extraction and purification from natural sources, e.g. cephalopods such as cuttlefish (e.g. *Sepia*) or squid (e.g. *Loligo*), bird feathers (e.g. from species with black strains such as Silkie chickens);
by chemical synthesis, whether water or non-water based e.g. (Deziderio, 2004) (daSilva et al., 2004; Lawrie et al., 2008; Pezzella et al., 2006);
by electrochemical synthesis, e.g. (Meredith et al., 2005);
by bioreactors created by utilization of natural or genetically altered bacteria, fungi, lichens, or viruses e.g. (della-Cioppa, 1998).

Cephalopod inks are natural composites of melanin with other materials, including peptidoglycans, amino acids, proteins, metals, and chemicals and enzymes (such as tyrosinase) which are involved in the synthesis of melanin, and other materials. Cephalopod inks include cuttlefish (such as *Sepia*), squid, and octopus inks. There is some variation among different species of the percentages of these components. Reports of cephalopod ink components include: Derby, C. D. 2014 Cephalopod Ink: Production, Chemistry, Functions and Applications Marine Drugs 12, 2700-2730; doi:10.3390/md12052700, and Magarelli M, Passamonti P, Renieri C. 2010. Purification, characterization and analysis of sepia melanin from commercial sepia ink (*Sepia officinalis*). Rev CES Med Vet Zootec; Vol 5 (2): 18-28.

Melanin Manufacturing and Fabrication

Melanin and melanin-like compounds can be manufactured as particles, nanoparticles, dust, beads, or fibers that are woven or non-woven e.g. by methods as described by (Greiner and Wendorff, 2007), sheets e.g. (Meredith et al., 2005), films (daSilva et al., 2004), plates, bricks, chars, spheres, nodules, balls, graphite-like sheets and shards, liquids, gels, or solids (e.g. thermoplastic or thermoset), and by common chemical engineering molding and fabrication methods or custom methods. Sheets can range from one molecular layer to several millimeters. Fibers can range from nanometers to several millimeters.

The melanin material may be natural or synthetic, with natural pigments being extracted from plant and animal sources, such as squid, octopus, mushrooms, cuttlefish, and the like. In some cases, it may be desirable to genetically modify or enhance the plant or animal melanin source to increase the melanin production. Melanins are also available commercially from suppliers.

The following procedure describes an exemplary technique for the extraction of melanin from cuttlefish (*Sepia officinalis*). 100 gm of crude melanin are dissected from the ink sac of 10 cuttlefish and washed with distilled water (3×100 ml). The melanin is collected after each wash by centrifugation (200×g for 30 minutes). The melanin granules are then stirred in 800 ml of 8 M Urea for 24 hours to disassemble the melanosomes. The melanin suspension is spun down at 22,000×g for 100 minutes and then washed with distilled water (5×400 ml). The pellet is washed with 50% aqueous DMF (5×400 ml) until a constant UV baseline is achieved from the washes. Finally, the pellet is washed with acetone (3×400 ml) and allowed to air dry.

Synthetic melanins may be produced by enzymatic conversion of suitable starting materials, as described in more detail hereinbelow. The melanins may be formed in situ within the porous particles or may be preformed with subsequent absorption into the porous particles.

Suitable melanin precursors include but are not limited to tyrosine, 3,4-dihydroxy phenylalanine (dopa), D-dopa, catechol, 5-hydroxyindole, tyramine, dopamine, m-aminophenol, o-aminophenol, p-aminophenol, 4-aminocatechol, 2-hydroxyl-1,4-naphthaquinone (henna), 4-methyl catechol, 3,4-dihydroxybenzylamine, 3,4-dihydroxybenzoic acid, 1,2-dihydroxynaphthalene, gallic acid, resorcinol, 2-chloroaniline, p-chloroanisole, 2-amino-p-cresol, 4,5-dihydroxynaphthalene 2,7-disulfonic acid, o-cresol, m-cresol, p-cresol, and other related substances which are capable of being oxidized to tan, brown, or black melanin-like compounds capable of absorbing ultraviolet radiation when incorporated in the polymeric particle matrix of the present disclosure. Combinations of precursors can also be used.

The melanin precursor is dissolved in an aqueous solution, typically at an elevated temperature to achieve complete solution. A suitable amount of the enzyme tyrosinase (EC 1.14.18.1) is added to the solution, either before or after the melanin precursor. The concentration of tyrosinase is not critical, typically being present in the range from about 50 to about 5000 U/ml. The solution is buffered with an acetate, phosphate, or other suitable buffer, to a pH in the range from about 3 to 10, usually in the range from about 5 to 8, more usually being about 7. Melanin-like pigments can be obtained using suitable precursors even in the absence of an enzyme just by bubbling oxygen through a solution of a precursor for an adequate period of time.

Melanin material may be obtained by treatment of, e.g, cuttlefish ink or squid ink in a microwave, optionally with mixing. The inventor has found that microwaving can be used for the preparation of melanin formulations. The compositions and methods as disclosed herein may be produced and practiced using a variety of heating techniques, such as, for example, infrared heating, microwave heating, convection heating, laser heating, sonic heating, or optical heating. For example, it was found that drying melanin in a microwave oven made possible the preparation of large amount of melanin from cuttlefish ink in a very short period of time. In an exemplary embodiment, cuttlefish ink at was placed at 40° C. in a conventional oven and required 18 days to reduce the material to 40% of its original weight. In a 900 watt microwave oven, the same degree of drying was achieved in 12 minutes. The disclosure provides a method for formulation of melanin by applying a hydraulic press to melanin partially dried in a microwave oven. In exemplary embodiments, hydraulic presses for this use may range in capacity from, for example, about 1 ton/sq. in. to about 500 tons/in$^2$ approximately. The disclosure provides a method wherein the hydraulic press applies compression of approximately 500 tons/in$^2$. In an exemplary embodiment, commercial cuttlefish ink was dried in a 900 watt microwave oven so that the product was 30% or 35% of the initial weight. A blender was used to mix and grind the melanin. A variety of formulations were made. In one formulation, the 30% preparation was mixed with 7% iron filings, and then the blender was used to mix again. In another formulation, 35% slabs were alternated with 30% slabs to create a layered composite. Each formulation was subjected to compression in a 20 ton/in$^2$ hydraulic press for about 20 minutes. Because the platen was approximately 3.5 in$^2$, it is estimated that a force of approximately 3265 pounds/sq. in. was exerted on each sample formulation.

The disclosure provides for the use of formulations of melanin produced by, for example, microwaving and hydraulic press compression to reduce penetration of bullets and other projectiles. The melanin produced by the methods of the disclosure proved effective in reducing the penetration of a bullet. In an exemplary embodiment, two slabs of melanin were produced by placing cuttlefish ink at 40° C. in a conventional oven and dried for 18 days to reduce the material to 40% of its original weight. In an alternative embodiment, cuttlefish ink was placed in a 900 watt microwave oven, and dried for 12 minutes to form two slabs. Each slab was approximately 3.5 in square. One slab was 1 inch thick and 1 slab was 0.5 in. thick. Both slabs were placed together in a wood frame to create a 1.5 inch thick sample of melanin. Several blocks of ballistic clay, approximately 3.5 in. square were placed behind the melanin sample. A control was created separately where the melanin sample was replaced by a (dummy) ballistic clay block. 9 mm bullets were fired at approximately 1200 ft/sec.

In the experimental setup, the bullet penetrated the melanin and then went a depth of approximately 6 cm into the clay. In the control setup the bullet penetrated the initial (dummy) clay block, and then penetrated 12 cm into the clay. This demonstrated that the melanin formulation showed effectiveness in reducing the bullet's penetration compared to the clay control.

The disclosure provides for the use of elemental metals mixed with melanin to create new formulations of melanin with novel properties. The metals may be, for example, iron, copper, zinc, cesium, radium, strontium, thorium, uranium, or combinations thereof. In an exemplary embodiment, elemental iron was mixed with melanin in the form of dried cuttlefish ink resulted in unexpected hardness of the material while it remains somewhat flexible. Under scanning electron microscopy it was demonstrated that the new formulation of melanin had organized into stacks of lamellae, which appeared to be composed of melanosomes. This is an entirely novel finding since, although metal ions are known to bind to the melanin, it does not appear that anyone has experimented with or reported that elemental iron can bind. This new disclosure is based on the finding that iron and other elemental metals including, for example, copper, zinc, cesium, radium, strontium, thorium, or uranium, can bind to melanin and organize it in novel ways which confer upon it new properties. For instance, the new properties conferred will include enhanced hardness, stiffness, impact resistance, electrical conductivity, capacitance, semiconductor properties, and enhanced ability to absorb radiation including x-ray and gamma ray.

In an exemplary embodiment, cuttlefish ink was dried using a microwave oven to 40% of its original weight. Iron filings were added so that they comprised 0.5% of the final formulation. The material felt harder than a similar sample without the 0.5% iron filings. Scanning electron microscopy revealed multiple areas where sharply defined lamellae with 900 corner angles were seen in stacks.

The disclosure provides a practical method for formulating melanin to be placed into pharmaceutical or dietary supplement capsules, and other containers. A novel method was developed to enable formulation of melanin (e.g., from cephalopod ink) into capsules or other containers for pharmaceutical, dietary supplement, and other uses. In an exemplary embodiment, cuttlefish ink was dried using a microwave oven to 40% of its original weight. Cab-O-Sil, a pharmaceutical preparation of the excipient micronized silicon dioxide, was mixed to comprise 40% of the final mixture with the 40% dried cuttlefish ink. This mixture was placed in a hard size zero pharmaceutical capsule. After seven days that the capsule became weak and flaccid and would be unsuitable for use. When the mixture of silicon dioxide and cuttlefish ink was dried for several days in a conventional oven at 40° C., then placed in the capsule and observed, the capsule remained intact and is suitable for human and animal use.

In some embodiments, melanins are incorporated into other materials and used for many useful applications, such as:

1. Melanin and melanin-like compounds can be incorporated into: polymers, metals, salts, ceramics of many types, clothing, construction materials, existing armor materials including Kevlar and ceramics, other natural materials or their synthetic mimics, materials for implantation into human or mammalian living beings.
2. A small percentage of melanin confers new or improved properties on resultant material: Another aspect of the present disclosure is that small amounts of melanin and of melanin-like substances will impart to a mixture of melanin with other substances, such as a matrix or polymer, properties which are unexpected. Generally, 1 to 5% of melanin will impart desired properties to a mixture or composite, whereas small incremental improvement in properties will be gained by increasing up to 35%. In exemplary embodies as disclosed herein, melanin may be present at about 1%, about 2%, about 3%, about 4%, about 5%, about 6%, about 7%, about 8%, about 9%, about 10%, at a range of about 1% to about 10%, at a range of about 2% to about 8%, at a range of about 3% to about 7%, at a range of about 1% to about 4%, at a range of about 2% to about 5%.

Examples of such unexpected properties are resistance to ultraviolet light, radiation, heat, flame, chemical agents and toxins, biological agents and toxins, and to abrasion.

3. Hydration effects and control: It is another aspect of the present disclosure that the control and maintenance of hydration of melanin and melanin like substances (or non-water solvent or matrix concentration for melanins made from organic solvents) is critical for the applications described above, including armor and shielding. Published research describes the effect of hydration on electrical conductivity, and on the ability to absorb radiation from the electromagnetic spectrum. The present disclosure includes the aspect that when melanin or melanin-like substances are extracted or synthesized, manufactured or fabricated, incorporated in any way with other substances, whether by mixtures, impregnation, layering, compositing, that control and maintenance of desired levels of hydration (and non-water solvent concentration for melanins made from organic solvents) may be critical to achieving and preserving the desired combination of properties. Much of the published research on melanin in the biological, chemical, physics, and electronics literature reports work done using commercially available melanin from Sigma-Aldrich Corp. (St. Louis, Missouri) which is prepared using lyophilization, thus dehydrating it. The present disclosure includes recognition that for the purposes set forth in this disclosure, such as armor and shielding, hydration and control of hydration may be critical for the properties desired in the final material, and the use of highly desiccated or lyophilized melanin may in many instances be undesirable. However, in certain aspects of the disclosure, desiccated or lyophilized melanin may be appropriate.

4. Oxygenation effects and control: It is another aspect of the present disclosure that the control and maintenance of oxygenation, or of lack of access to oxygen, by incorporating melanin into materials that control this factor, or by restricting use to environments that control or restrict this factor, may be critical for certain characteristics to be achieved for shielding, armor, flame retardancy, heat resistance, and cold resistance.

5. Incorporation methods for melanin into other materials includes, for example: mixtures, covalent or non-covalent binding, printing, stamping, electrochemical deposition, metallic salt binding, adhering, and layering in composites.

In certain embodiments, the compositions and methods of the disclosure may be produced or practiced using molding techniques such as transfer molding, resin film infusion, resin transfer molding, and structural reaction injection molding (SRIM). In certain embodiments, the compositions and methods of the disclosure may be produced or practiced using molding techniques such as a vacuum assisted resin transfer molding process (VAR™).

Composites

Process aids and modifiers are materials commonly used to facilitate polymer fabrication, to help compatibilize the mixture of polymers, ceramics, and other additives, and the like, to increase fire resistance, or to modify other properties, other than primary ballistic protection properties. Any of these material that are desirable for fabricating or using the new lightweight ballistic protection materials may be incorporated into the current disclosure, including but not limited to materials such as silicones, phthalates, bromides, and the like.

Other additives, present in amounts not exceeding 10% by weight, if any, may also be included. These materials may include, but are not limited to adhesion aides, colorants, fibers (carbon, polyaramid, polyethylene, etc.), fillers (talc, sand, microballoons) that further serve to modify the process-ability, stability, durability, or appearance of the objective ballistic protection materials.

Any suitable ceramic materials may be used in the composite composition in accordance with the current disclosure. In one embodiment the ceramic powders or particles may be selected from the group consisting of alumina, boron carbide, boron nitride, mullite, silica, silicon carbide, silicon nitride, magnesium boride, multi-walled carbon nanotubes, single walled carbon nanotubes, group IVB, VB and VIB metal sulfide nanotubes, titanium boride, titanium carbide, and diamond.

The current disclosure is also directed to methods of preparing ballistic protection materials. In one embodiment, the ballistic protection material is formed by a simple process of mixing the starting materials without melt processing prior to the final molding step. This simplifies the processing, as it is not necessary to undertake the possibly complicated step of melt processing with its accompanying difficulties in dispersion and equipment wear.

Although such a simple mixing process may be used, other processes for forming the ballistic protection material of the current disclosure can also be utilized. These include melt compounding, in which the ceramic and the polymer are intimately mixed while the polymer is in the molten state. In this embodiment the mixing can be done in any suitable standard machinery such as single and twin-screw extruders (both co- and counter-rotating), Henschel mixers, co-kneaders, etc. An additional technique that can be used is solvent mixing in which the ceramic and the polymer are mixed while the polymer is dissolved in the appropriate solvent. In such an embodiment any suitable solvent may be utilized.

The current disclosure is also directed to articles made with the ballistic protection material in accordance with the above processes. Ballistic protection materials of the present disclosure may be fabricated into any suitable article, including but not limited to sheets, slabs, disks, or more complex shapes, of varying thicknesses and sizes.

Using such construction techniques, the ballistic protection materials of the present disclosure may be used together with other ballistic materials, including but not limited to woven ballistic fabrics (such as but not limited to polyaramid or polyethylene fabrics), metals, ceramics, and the like to form ballistic protection articles, such as, for example, helmets, sheets or panels, or body armor. In another example, body armor using the inventive material may be fabricated by first forming a woven fiber vest containing pockets then sewing flat or curved panels or tiles comprising the composite into the pockets. The sheets or panels may also be incorporated into a number of blast or ballistic shields or armor, such as, for example, blast/ballistics shields or armor for vehicles, aircraft and watercraft like cars, trucks, vans, personnel carriers, limousines, trailers, helicopters, cargo planes, rail cars, boats and ships; armor or blast/ballistic protection for small buildings, especially military command posts and mobile headquarters; armor or blast/ballistic protection for cargo containers; armor or blast/ballistic protection for equipment housing, such as, for example, computers, communications equipment; and generally mobile or stationary blast or ballistic protection panels.

In an embodiment, a structure is provided. The structure includes bonded alternating layers of at least a melanin material and at least one of a fibrous sheet, a plastic sheet, a plastic plate, a ceramic sheet, a ceramic plate, and a multilayer ply, the multilayer ply comprising multiple fibrous sheets bonded together.

In another embodiment, a structure is provided. The structure includes alternating layers of melanin material wherein said layers are bonded to each other.

In another embodiment, a structure is provided. The structure includes alternating layers of melanin material wherein said layers are joined to each other by an array of oriented nanostructures.

In yet another embodiment, a method for fabricating a melanin composite is provided. The method includes providing a first layer, the layer comprising at least a fibrous sheet or a multilayer laminate; applying a second layer to the first layer, the layer comprising an melanin material; applying a third layer to the second layer, the layer comprising another fibrous sheet or multilayer laminate; bonding or joining the first layer to the second layer; and bonding or joining the second layer to the third layer.

In another embodiment, a method for fabricating a melanin composite is provided. The method includes providing a first layer, the layer comprising at least a fibrous sheet or a multilayer laminate; applying a second layer to the first layer, the layer comprising a liquid-phase gel precursor; applying a third layer to the second layer, the layer comprising another fibrous sheet or multilayer laminate; bonding or joining the first layer to the second layer; and bonding or joining the second layer to the third layer.

In yet another embodiment, a method for fabricating a melanin composite is provided. The method includes providing two layers of melanin material, and bonding the two layers together.

In another embodiment, a method for fabricating a melanin composite is provided. The method includes providing a liquid-phase; forming a gel from the liquid-phase precursor; and optionally forming a second gel in contact with the first gel.

In an embodiment, a composition is provided. The composition includes melanin and non-melanin material, and embedding the melanin material within the non-melanin material.

Biological Polymers

The term "biological polymer" according to the disclosure, it is understood collagen and its derivatives, hyaluronic acid, its salts and its derivatives, alginates, synthetic polymers, elastin and biological polymers, and mixtures thereof. Preferably, the biological polymer may comprises compounds chosen from collagen, collagen of porcine origin, collagen of bovine origin, crosslinked collagens, hyaluronic acid, its salts and its derivatives, lactic acid polymers, methacrylate derivatives, calcium phosphate derivatives, polyacrylamides, polyurethanes, polyalkylimide gels, polyvinyl microspheres, silicones, silica ($SiO_2$) polymers, and mixtures thereof.

Collagen is a fibrous protein, of approximately 300 kDa, which makes up the connective tissue in the animal kingdom. It may be of human or nonhuman origin, in particular of porcine or bovine origin. Collagen derivatives include, inter alia, crosslinked collagens.

The composites of the disclosure may be formed from a wide variety of polymers, including natural polymers such as carboxylmethylcellulose, cellulose acetate phthalate, ethylcellulose, methylcellulose, arabinogalactan, nitrocellulose, propylhydroxycellulose, and succinylated gelatin; and synthetic polymers such as polyvinyl alcohol, polyethylene, polypropylene, polystyrene, polyacrylamide, polyether, polyester, polyamide, polyurea, epoxy, ethylene vinyl acetate copolymer, polyvinylidene chloride, polyvinyl chloride, polyacrylate, polyacrylonitrile, chlorinated polyethylene, acetal copolymer, polyurethane, polyvinyl pyrrolidone, poly(p-xylene), polymethylmethacrylate, polyvinyl acetate, polyhydroxyethyl methacrylate, and combinations thereof.

Utility and Characteristics

The following characteristics and functions for armor, shielding and other applications can be achieved, in almost infinite variety of degrees and combinations:

Protection from Weapons

It is another aspect of the present disclosure that melanin and composite materials incorporating melanin can be used for shielding from biological, chemical, radiological and nuclear weapons.

It is another aspect of the present disclosure that melanin and composites materials incorporating melanin can be used for shielding from impact due to bullets or other projectiles or explosives, including shaped charges.

The current disclosure is directed to a ballistic protection material composition comprising one or more type of, e.g., ceramic powders or particles mixed with one or more type of melanin materials.

In one embodiment, in addition to the melanin material, other polymeric materials may be further selected from the group consisting of rigid-rod polymers, semi-rigid-rod polymers, polyimides, polyetherimides, polyimideamides, polysulfones, epoxy resins, bismaleimide resins, bis-benzocyclobutene resins, phthalonitrile resins, polyaryletherketones, polyetherketones, liquid crystal polymers, oligomeric cyclic polyester precursors, polybenzbisoxazoles, polybenzbisthiazoles, polybenzbisimidazoles, acetylene endcapped thermosetting resins, PrimoSpire® polymers, polysulfones, polyaramides, poly-paraphenylene terephthalamide, polyamides, polycarbonates, polyethylenes, polyesters, polyphenols and polyurethanes.

In another embodiment, the composition further comprises one or more types of process aids, modifiers, colorants, fibers, adhesion promoters and fillers.

In still another embodiment, ceramic powders or particles are selected from the group consisting of alumina, boron carbide, boron nitride, mullite, silica, silicon carbide, silicon nitride, magnesium boride, multi-walled carbon nanotubes, single walled carbon nanotubes, group IVB, VB and VIB metal sulfide nanotubes, titanium boride, titanium carbide, and diamond.

In yet another embodiment, ceramic powders or particles provide 10% to 98% of the total mass, in a preferred embodiment the ceramic powders or particles provide 20% to 95% of the total mass, and in a most preferred embodiment the ceramic powders or particles provide at least 50% of the total mass.

In still yet another embodiment, ceramic powders or particles have particle size in the range of 10 nanometers to 100 microns; and in a preferred embodiment the ceramic powders or particles have particle size in the range of 100 nanometers to 10 microns.

In still yet another embodiment, the melanin material or materials provide 2% to 95% of the total mass, and in a preferred embodiment the melanin material or materials provide less than 50% of the total mass.

In still yet another embodiment, the ballistic protection materials are used together with other ballistic materials, including, but not limited to woven ballistic fabrics (such as but not limited to polyaramid or polyethylene fabrics), metals, ceramics, and the like.

In still yet another embodiment, the ballistic protection materials are incorporated into an article selected from the group consisting of: a ballistic protection article, a helmet, a sheet or panel, such as a vehicle or blast protection panel, body armor, and cargo containers.

Protection from Lasers

It is another aspect of the present disclosure that melanin and composite materials including melanin can be used for shielding from lasers.

Thermal Properties

Melanin's ability to resist degradation by extreme heat, e.g. >500° C., was reported by Deziderio (Deziderio, 2004). Melanin's ability to resist degradation by extreme cold (slightly above absolute zero) was reported by (Yang and Anderson, 1986). The present disclosure includes the discovery that melanin can be used alone, or in composites with other materials such as metals and polymers, to resist destruction by high heat or temperature, for shielding, armor, and aerospace applications such as airplane and space vehicle construction parts.

Chemical Properties

The ability of melanin to resist degradation by chemicals of all types, including strong acids (such as hydrochloric acid) and bases (such as sodium hydroxide), was reviewed by (Prota, 1992). The present disclosure includes the discovery that melanin can be used alone, or in composites with other materials such as metals and polymers, to resist destruction by chemicals including strong acids and strong bases, for shielding, armor, and aerospace applications such as airplane and space vehicle construction parts.

Protection from Radiation

It has been reported that melanin absorbs beta particles, gamma rays, X-rays, infrared, visible, ultraviolet, and the remainder of the electromagnetic spectrum.

The present disclosure includes the discovery that melanin can be used alone, or in composites with other materials such as lead and polymers, to absorb and prevent destruction by radiation, e.g. for shielding, armor, and aerospace applications such as airplane and space vehicle construction parts.

The present disclosure includes the discovery that melanin can be used alone, or in composites with other materials for:
a. shielding of radiation from sources like uranium and radium.
b. to degrade, encapsulate and shield from living and non-living radioactive particles in sizes from nanometers to millimeters.
c. to shield personnel and equipment from radiation from depleted uranium used in weaponry or armor.

The present disclosure includes the discovery that melanin can be used alone, or in composites with other materials not only by covering a human or other organism by melanin and melanin-like compounds, alone or in mixture with other materials: It can be accomplished by ingestion, injection, or other internal administration of these compounds or composites.

Furthermore, the melanin or melanin-like compounds, can be used to mitigate the destructive biological effects of radiation, even if the radiation has been absorbed. For instance, radiation creates free radicals in biological tissues which creates great damage in the hematopoietic and gastrointestinal systems. Melanin and melanin like compounds are known to absorb such free radicals and mitigate such damage.

Shielding from Micro-Organisms and Infectious Agents

The present disclosure includes the discovery that melanin can be used alone, or in composites with other materials to form a physical barrier against microorganisms and infectious agents of all types including: bacteria, fungi, parasites, viruses.

Protection from Adherence

The present disclosure includes the discovery that melanin can be used alone, or in composites with other materials to form shielding from adherent substances for applications where Teflon and similar materials are currently used.

Protection from Sensors

The present disclosure includes the discovery that melanin can be used alone, or in composites with other materials to form shielding from electromagnetic, sound, ultrasound, and radar sensors.

Use in Armor and Aerospace

Melanin has been reported to be hard (Majerus, 1998) and to resist abrasion (Majerus, 1998; Moses et al., 2006) The present disclosure includes the discovery that melanin can be used alone, or in composites with other materials to form body armor, vehicle armor, and other applications, including aerospace use, where desirable characteristics include hardness, resistance to abrasion, resistance to indentation, resistance to cutting, flexibility, shock absorption, and sound and ultrasound absorption.

Electrical Properties

The present disclosure includes the discovery that melanin can be used alone, or in composites with other materials, in harsh environments such as the vacuum and extreme cold of space where the following listed properties are desirable or necessary:

Photoconductivity (when light is shined on it, electricity flows),
Semiconductor properties,
Electricity conduction, and
Paramagnetism (Nordlund, 2006).

Binding to Metals and Radioactive Substances

It has been reported that melanin binds to metals and radioactive substances (Bruenger et al., 1967) (Fogarty and Tobin, 1996) (Kasatna et al, 2003) (Taylor et al., 1964). The present disclosure includes the discovery that melanin can be used alone, or in composites with other materials to form shielding and armor and for aerospace applications, specifically because it naturally binds to a wide range of metals and to radioactive substances.

Binder

Binders are useful in fabricating materials from non or loosely assembled matter. For example, binders enable two or more surfaces to become united. In certain embodiments, non-melanin material may be included in the compositions and methods of the disclosure and may be a binder. In exemplary embodiments, any adhesive material, such as phenolic resins, urea-formaldehyde resins, melamine formaldehyde resins, hyde glue, aminoplast resins, epoxy resins, acrylate resins, latexes, polyester resins, urethane resins, and mixtures thereof may be used as a binder. Suitable binders include glue, varnish, epoxy resins, phenolic resins, polyurethane resins. In exemplary embodiments, the binder may be, for example, glue, which may be selected from the group consisting of Clear Weld, LOCTITE® Heavy Duty Epoxy, LOCTITE® Epoxy-Metal/Concrete, LOCTITE INSTANT-MIX®, LOCTITE®, LOCTITE® BULLDOG, LOCTITE® PL Marine Adhesive Sealant, E6000@, (E6000 STITCH-LESS®, E6000 EXTREME TACK®, E6000 FABRI-FUSE®, PRO-POXY® 20, TITEBOND III®, TITEBOND III ULTIMATE WOOD GLUE®, FIBER FIX SUPER TAPE, ELMER'S SCHOOL GLUE NATURALS®, ELMER'S GLUE-ALL®, Elmer's Multi Purpose All Glue, KRAZY GLUE®, LIQUID NAILS®, PRO-DUTY® HEAVY DUTY CONSTRUCTION ADHESIVE, Firmo Liquid, Welbond Universal Adhesive, and combinations thereof.

Thermally curable resins suitable for use in accordance with the compositions and methods of the disclosure are preferably selected from the group consisting of phenolic resins, urea-formaldehyde resins, melamine-formaldehyde resins, epoxy resins, acrylate resins, urethane resins, melamine resins, alkyd resins, and polyimide resins, isocyanate, isocyanurate, and combinations thereof. Multifunctional acrylates are preferably selected from trimethylolpropane triacrylate, glycerol triacrylate, pentaerythritol triacrylate and methacrylate, pentaerythritol tetraacrylate and methacrylate, dipentaerythritol pentaacrylate, sorbitol triacrylate, and sorbital hexaacrylate.

Thermoplastic binders comprise a variety of polymerized materials such as polyvinyl acetate, polyvinyl butyral, polyvinyl alcohol, and other polyvinyl resins; polystyrene resins; acrylic and methacrylic acid ester resins; cyanoacrylates; and various other synthetic resins such as polyisobutylene polyamides, courmarone-idene products, and silicones.

Suitable functionalized acrylics, alkyds, polyurethanes, polyesters, and epoxies can be obtained from a number of commercial sources. Useful acrylics are sold under the ACRYLOID™ trade name (Rohm & Haas, Co., Pennsylvania); useful epoxy resins are sold under the EPON™ trade name (Resolution Specialty Materials, LLC, Illinois); useful polyester resins are sold under the CYPLEX® trade name (Cytec Industries, New Jersey); and useful vinyl resins are sold under the UCAR™ trade name (The Dow Chemical Company, Michigan).

Illustrative of useful high modulus or rigid binder materials are polycarbonates; polyphenylenesulfides; polyphenylene oxides; polyester carbonates; polyesterimides; polyimides; and thermoset resins such as epoxy resins, phenolic resins, modified phenolic resins, allylic resins, alkyd resins, unsaturated polyesters, aromatic vinylesters as for example the condensation produced of bisphenol A and methacrylic acid diluted in a vinyl aromatic monomer (e.g. styrene or vinyl toluene), urethane resins and amino (melamine and urea) resins. The major criterion is that such material holds the composition together, and maintains the geometrical integrity of the composite under the desired use conditions.

The binder can be included in the composition in any suitable amount. For example, the binder can be included in an amount from about 5 wt. % to about 100 wt. % by weight (on a solids basis) of the wet composition, such as from about 20 wt. % to about 80 wt. %, from about 30 wt. % to about 70 wt. %, from about 40 wt. % to about 60 wt. %, etc.

Pharmaceutical Formulations

The disclosure provides a practical method for formulating compositions comprising melanin to be placed into pharmaceutical or dietary compositions. The disclosure provides a practical method for formulating melanin to be placed into pharmaceutical or dietary supplement capsules, and other containers. A novel method was developed to enable formulation of melanin (e.g., from cephalopod ink) into capsules or other containers for pharmaceutical, dietary supplement, and other uses. In an exemplary embodiment, cuttlefish ink was dried using a microwave oven to 40% of its original weight. Cab-O-Sil, a pharmaceutical preparation of the excipient micronized silicon dioxide, was mixed to comprise 40% of the final mixture with the 40% dried cuttlefish ink. This mixture was placed in a hard size zero pharmaceutical capsule. After seven days that the capsule became weak and flaccid and would be unsuitable for use. When the mixture of silicon dioxide and cuttlefish ink was dried for several days in a conventional oven at 40° C., then placed in the capsule and observed, the capsule remained intact and is suitable for human and animal use.

The compositions of the disclosure may be administered enterally or parenterally. Mixed with pharmaceutically suitable auxiliaries, e.g., as described in the standard reference, Gennaro et al., Remington's Pharmaceutical Sciences. The compositions may be compressed into solid dosage units, such as pills, tablets, or be processed into capsules or suppositories. By means of pharmaceutically suitable liquids the compositions can also be applied in the form of a solution, suspension, emulsion, e.g. for use as an injection preparation or eye drops, or as a spray, e.g. for use as a nasal spray.

For making dosage units, e.g., tablets, the use of conventional additives such as fillers, colorants, polymeric binders and the like is contemplated. In general, any pharmaceutically acceptable additive which does not interfere with the function of the active compounds can be used. Suitable carriers with which the compositions can be administered include lactose, starch, cellulose derivatives and the like, or mixtures thereof, used in suitable amounts.

Pharmaceutical Dosage Forms

The compositions of the present disclosure can be processed by agglomeration, air suspension chilling, air suspension drying, balling, coacervation, coating, commination, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, a capsule, a tablet, an implant, a troche, a lozenge (minitablet), a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate, a platelet, a strip or a sachet. Compositions can also be administered as a "dry syrup", where the finished dosage form is placed directly on the tongue and swallowed or followed with a drink or beverage. These forms are well known in the art and are packaged appropriately. The compositions can be formulated for oral, nasal, buccal, ocular, urethral, transmucosal, vaginal, topical or rectal delivery.

The pharmaceutical composition of the disclosure can be coated with one or more enteric coatings, seal coatings, film coatings, barrier coatings, compress coatings, fast disintegrating coatings, or enzyme degradable coatings. Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E100, may be particularly suitable for taste masking applications. Traditional enteric coating materials listed elsewhere can also be applied to form an isolating layer.

Extended release coatings are designed to effect delivery over an extended period of time. The extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery to both the small and large intestines, to only the small intestine, or to only the large intestine, depending upon the choice of coating materials and/or coating thickness.

Enteric coatings are mixtures of pharmaceutically acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent. Additional additives and their levels, and selection of a primary coating material or materials will depend on the following properties: 1. resistance to dissolution and disintegration in the stomach; 2. impermeability to gastric fluids and drug/carrier/enzyme while in the stomach; 3. ability to dissolve or disintegrate rapidly at the target intestine site; 4. physical and chemical stability during storage; 5. non-toxicity; 6. easy application as a coating (substrate friendly); and 7. economical practicality.

Delayed release generally refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present disclosure to achieve delivery to the lower gastrointestinal tract. Polymers for use in the present disclosure are anionic carboxylic polymers.

Shellac, also called purified lac, a refined product obtained from the, resinous secretion of an insect. This coating dissolves in media of pH>7.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

In carrying out the method of the present disclosure, the compositions of the disclosure may be administered to mammalian species, such as dogs, cats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like.

The dose administered must be carefully adjusted according to age, weight and condition of the patient, as well as the route of administration, dosage form and regimen and the desired result.

The pharmaceutical compositions of the disclosure may be administered in the dosage forms in single or divided doses of one to four times daily. It may be advisable to start a patient on a low dose combination and work up gradually to a high dose combination.

Tablets of various sizes can be prepared, e.g., of about 1 to 2000 mg in total weight, containing one or both of the active pharmaceutical ingredients, with the remainder being a physiologically acceptable carrier of other materials according to accepted pharmaceutical practice. These tablets can be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonful.

Dosage forms can be administered to the patient on a regimen of, for example, one, two, three, four, five, six, or other doses per day.

In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

In formulating the compositions, the active substances, in the amounts described above, may be compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

One embodiment of this disclosure includes methods of treating, preventing, or diagnosing a particular disease or condition by administering the disclosed compositions to a subject. In many instances, the compositions can be administered alone or can be included within a pharmaceutical composition. An effective amount of a pharmaceutical composition, generally, is defined as that amount sufficient to ameliorate, reduce, minimize, or limit the extent of the disease or condition. More rigorous definitions may apply, including elimination, eradication, or cure of the disease or condition.

The composition may be in nanoparticulate form. "Nanoparticles" are solid particles of an average particle diameter of, for example, less than about 1 micron (micrometer). One micron is 1,000 nanometers (nm). "Stabilized" nanoparticles are nanoparticles coated with a stabilizing material and having a reduced tendency for aggregation and loss of dispersion with respect to nanoparticles of the compound of the disclosure without a stabilizing coating. A nano-spray is a spray containing nanoparticles or a spray that produces nanoparticles. A nanodispersion is a dispersion containing nanoparticles. A nanosuspension is a suspension containing nanoparticles.

The liquid formulations useful herein may comprise a solvent, solution, suspension, microsuspension, nanosuspension, emulsion, microemulsion, gel or even a melt containing the active component or components. In some embodiments the nanoparticles, nanofibers, or nanofibrils may be in the form of, or within or on, granules, powders, suspensions, solutions, dissolvable films, mats, webs, tablets, or releasable forms particularly releasable dosage forms. Other particular useful forms are concentrates to which a diluting liquid is added prior to use. The product may also be sprayed onto the inner surface of a container to which a liquid is added later prior to use and the nanoparticles, nanofibers, or nanofibrils, are released into the liquid.

Pharmaceutical compositions of the present disclosure can include nanoparticles, composite nanoparticles, nanosuspension, or nanocapsules of the present disclosure.

The composition may also include various antioxidants to retard oxidation of one or more active ingredient or nanoparticles, composite nanoparticles, nanosuspension, or nanocapsules. The prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In order to increase the effectiveness of a treatment with the nanoparticles, nanogels, composite nanoparticles, nanosuspension, or nanocapsules of the present disclosure, it may be desirable to combine these nanoparticles, composite nanoparticles, or nanocapsules with other therapies effective in the treatment of a particular disease or condition.

The formulations as described above may be administered for a prolonged period, that is, for as long as the potential for a disease or condition remains or the symptoms continue.

Pharmaceutical Packaging/Treatment Kits

The present disclosure relates to a kit for conveniently and effectively carrying out the methods in accordance with the present disclosure. Such kits may be suited for the delivery of solid oral forms such as tablets or capsules. Such a kit may include a number of unit dosages. Such kits can include a means for containing the dosages oriented in the order of their intended use. An example of a means for containing the dosages in the order of their intended uses is a card. An example of such a kit is a "blister pack". Blister packs are well known in the packaging industry and are widely used for packaging pharmaceutical unit dosage forms. If desired, the blister can be in the form of a childproof blister, i.e., a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid day" and a PM dose; or an AM dose is packaged with a PM dose. Alternatively, placebo dosages, or vitamin or dietary supplements, either in a form similar to or distinct from the pharmaceutical active dosages, can be included.

In one aspect, the package, kit or container comprises a "blister package" (also called a blister pack, or bubble pack). In one aspect, the blister package consists two or more separate compartments: Am dosage of this disclosure, and PM dosage of this disclosure, or mid-day dosage of this disclosure. This blister package is made up of two separate material elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

As discussed herein, the products of manufacture of the disclosure can comprise the packaging of the therapeutic drug combinations of the disclosure, alone or in combination, as "blister packages" or as a plurality of packettes, including as lidded blister packages, lidded blister or blister card or packets, or a shrink wrap.

Other means for containing said unit dosages can include bottles and vials, wherein the bottle or vial comprises a memory aid, such as a printed label for administering said unit dosage or dosages. The label can also contain removable reminder stickers for placement on a calendar or dayminder to further help the patient to remember when to take a dosage or when a dosage has been taken.

REFERENCES

Bettinger, C. J., Bruggeman, J. P., Misra, A., Borenstein, J. T., and Langer, R., 2009. Biocompatibility of biodegradable semiconducting melanin films for nerve tissue engineering. Biomaterials 30, 3050-3057.

Bruenger, F. W., Stover, B. J., and Atherton, D. R., 1967. The Incorporation of Various Metal Ions into in Vivo- and in Vitro-Produced Melanin. Radiation Research 32, 1-12.

daSilva, M., Deziderio, S. N., and Gonzalez, J. C., 2004. Synthetic melanin thin films: Structural and electrical properties. J. Appl. Phys. 96, 5803-5807.

della-Cioppa, G. et al., 1998 Melanin production from transformed *Escherichia coli,* 1998. U.S. Pat. No. 5,837, 505. Patent Issue Date: Nov. 17, 1998

Deziderio, S., 2004. Thin films of synthetic melanin. Journal of Non-Crystalline Solids 338-340, 634-638.

Fogarty, R. V., and Tobin, J. M., 1996. Fungal melanins and their interactions with metals. Enzyme Microb Technol 19, 311-7.

Greiner, A., and Wendorff, J. H., 2007. Electrospinning: A Fascinating Method for the Preparation of Ultrathin Fibers. Angewandte Chemie International Edition 46, 5670-5703.

Kasama, T., Murakami, T., and Ohnuki, T., Accumulation Mechanisms of Uranium, Copper and Iron by *Lichen Trapelia involuta,* in: Kobayashi, I. And Ozawa, H., Eds.), Biomineralization (BIOM2001): formation, diversity, evolution and application, Proceedings of the 8th International Symposium on Biomineralization, Tokai Univ. Press 2003.

Lawrie, K. J., Meredith, P., and McGeary, R. P., 2008. Synthesis and Polymerization Studies of Organic-Soluble Eumelanins. Photochemistry and Photobiology 84, 632-638.

Majerus, M. E. N., 1998. Melanism. Oxford University Press, New York.

Meredith, P., Subianto, S., and Will, G., 2005. Process For The Production Of Thin Films Of Melanin And Melanin- Like Molecules By Electrosynthesis, in: World Intellectual Property Organization Application No. WO 2005/026216 A1.

Moses, D. N., Mattoni, M. A., Slack, N. L., Waite, J. H., and Zok, F. W., 2006. Role of melanin in mechanical properties of Glycera jaws. Acta Biomater 2, 521-30.

Nordlund, J. J., 2006. The pigmentary system: physiology and pathophysiology. Blackwell Pub., Malden, Mass.

Pezzella, A., Panzella, L., Crescenzi, O., Napolitano, A., Navaratman, S., Edge, R., Land, E. J., Barone, V., and d'Ischia, M., 2006. Short-Lived Quinonoid Species from 5,6-Dihydroxyindole Dimers en Route to Eumelanin Polymers: An Integrated Chemical, Pulse Radiolytic, and Quantum Mechanical Investigation. Journal of the American Chemical Society 128, 15490-15498.

Povlich, L. K., Le, J., Kim, J., and Martin, D. C., 2010. Poly(5,6-dimethoxyindole-2-carboxylic acid) (PD-MICA): A Melanin-Like Polymer with Unique Electrochromic and Structural Properties. Macromolecules 43, 3770-3774.

Prota, G., 1992. Melanins And Melanogenesis. Academic Press, New York. Taylor, G. N., Stover, B. J., Jee, W. S., and Mays, C. W., 1964. Selective Deposition of Radium in Normal and Neoplastic Melanocytes. Radiat Res 21, 285-98.

Yang, I. S., and Anderson, A. C., 1986. Specific heat of melanin at temperatures below 3 K. Physical Review B 34, 2942.

The disclosure will be illustrated in more detail with reference to the following Examples, but it should be understood that the present disclosure is not deemed to be limited thereto.

EXAMPLES

Example 1—Test Results

A controlled experiment was conducted to see whether slabs (plates) of melanin would retard bullets.

Preparation of Prototype Armor Plates

The slabs were about 3.75"×3.75"×0.75". Wax (Paraplast from Leica Biosystems, Buffalo Grove, IL) and Polyethylene Glycol 20,000mw (PEG) from Sigma-Aldrich, of St. Louis, MO, were matrix materials used as controls, and to encase or mix with the melanin in the experimental slabs. The source of the melanin was commercial cuttlefish ink, which is approximately 20% melanin, 5% protein, and 75% water. The ink was partially dehydrated by various methods, and then mixed with a matrix or and/or encased in a matrix as follows. The purpose was to determine whether any method of dehydration and preparation was superior for the purpose of retarding bullets.

| Slab # | Description |
| --- | --- |
| 101 | Control - Wax |
| 102 | Control - PEG |
| 103 | Centrifuged Melanin, mixed with PEG, enclosed in Wax |
| 104 | Centrifuged Melanin, mixed with PEG, enclosed in Wax |
| 105 | Centrifuged/Evaporated Melanin, mixed with PEG, enclosed in Wax |
| 106 | Centrifuged/Evaporated Melanin, Sandwiched in PEG |
| 107 | Centrifuged/Evaporated Melanin, Sandwiched in PEG |
| 108 | Microwaved Melanin, Sandwiched in Wax |

For slabs 103 and 104, cuttlefish ink (CI) was centrifuged at 2900 g, resulting in melanin which was about 20% by weight of the original CI. It was then mixed with PEG in a 70% Melanin: 30% PEG ratio, and enclosed in a thin layer of wax.

For slabs 105, 106 and 107, the cuttlefish ink was first centrifuged at 2900 g to 50% of its original weight, and that melanin sediment was then evaporated at 45° C. by another 50%, resulting in melanin that was about 25% by weight of the original cuttlefish ink. For slab 105, the melanin was then mixed with PEG in a (70% Melanin: 30% PEG) ratio, and enclosed in a thin layer of wax. For slabs 106 and 107, the melanin was sandwiched between layers of PEG.

For slab 108 the cuttlefish ink was microwaved on high for about 10 minutes with mixing every 2-3 minutes. It was then sandwiched between wax layers.

Testing Methods and Materials

For testing, 9 mm bullets were fired from a Beretta M9 handgun.

The gun was mounted on a "Ransom Rest" apparatus (Ransom International Corp, Prescott Valley, AZ), which permits precise immobilization of the gun, aiming, and firing. To measure the velocities of the bullets, a chromatograph (Prochrono Digital by Competition Electronics, Rockford, IL) was used. An initial test was done in which 5 individual bullets' velocities were measured and this gave an average velocity of 1194.2 ft/sec and a small standard deviation of 11.4 ft/sec. The test slab was placed 10 ft. from the gun.

A testing device was constructed composed of a wooden frame with 5 clay slabs (each about 3.75"×3.75"×1"), where the clay slabs were separated by paper index cards. Behind the set of clay slabs was a set of clay blocks, with a depth of abut 2". This made for a total of approximately 7" of clay through which the bullet could traverse.

For testing, one or two melanin slabs, as listed below, were attached to the front of the first clay slab in the testing device. (When we had 2 slabs of the same composition and preparation, they were placed together so that the bullet would traverse 2 slabs.)

Slabs 103 and 104 were attached together and tested with one shot.

Slabs 106 and 107 were attached together and tested with one shot.

All of the other slabs were tested singly.

Results

Controls

The bullet went through all the way through the clay slabs and was lost, for each of the controls, one of wax and one of PEG.

Experimental

For all of the remaining slabs, the bullet penetrated through the melanin slab(s) and then was found at 3"-4" in the clay. The best performance was by the single microwaved melanin slab.

Conclusion

All of the prototype armor plates composed of melanin significantly retarded the bullet so that it was retained in the clay backing, whereas all the control plates failed to retard the bullet so that it blasted entirely through the clay backing.

Example 2—Body Armor

For example, melanins used in body armor, will have one or more the following properties:
- hardness,
- resistance to abrasion,
- resistance to impact,
- tensile strength,
- absorption of biological toxins,
- absorption of chemical toxins,
- absorption of radiation,
- resistance to heat,
- resistance to cold,
- resistance to ultraviolet light,
- resistance to fungal, bacterial, viral and plant contamination and degradation, flexibility, and
- as well as needed: photoconductivity, semiconductor functions, and electrical conductivity.

The degree of each of the functions above can be set and adjusted by controlling and maintaining the hydration of melanins or by controlling and maintaining the non-water solvent or matrix concentration for melanins made from organic solvents.

Example 3—Flame Retardancy and Heat Resistance

Some melanins (e.g. synthetic melanins made with organic solvents, such as reported by Deziderio, 2004) have greater flame retardancy and heat resistance in environments where oxygen is not present. Therefore, one method of creating a material with extreme heat resistance would be to bind by chemical or electrodeposition means melanin to layers of flame retardant materials, or metals with high melting points, such that melanin is protected from oxygen in the composite materials environment. Because melanin is lightweight and relatively inexpensive, it would result in lighter and cheaper composites than the matrix alone. The outer flame retardant or metals could be only a few molecular layers thick.

A related example is the use of melanins in vacuums such as outer space, or thin earth atmosphere, where little or no oxygen is present. A third example would be use of melanin or composites with melanin in environments with inert gases such as argon or nitrogen.

Example 4—Protection of Military Personnel from Depleted Uranium Radiation

Depleted uranium is used both in munitions and in armor (because of its great density). Personnel handling such items are subject to medical problems from radiation exposure. Melanin naturally binds to uranium (Kasama et al., 2003). Therefore it could be either incorporated into the main uranium matter or used as a coating around it to protect personnel. Also personnel could wear protective clothing made with melanin shielding to protect them from the radiation.

Example 5. Microwave Preparation of Melanin Formulations

It was found that drying melanin in a microwave oven made possible the preparation of large amount of melanin from cuttlefish ink in a very short period of time.

Cuttlefish ink at was placed at 37° C. in a conventional oven and required 7 days to reduce the material to 40% of its original weight. In a 900 watt microwave oven, the same degree of drying was achieved in 12 minutes.

2. Use of Hydraulic Presses to Create New Formulations of Melanin.

A new method for formulation of melanin were created by applying a hydraulic press to melanin partially dried in a microwave oven. In exemplary embodiments, the hydraulic presses for this use may range in capacity from approximately 1 ton/in$^2$ to 500 tons/in$^2$, 1 ton/in$^2$ to 50 tons/in$^2$, 50 tons/in$^2$ to 100 tons/in$^2$, 1 ton/in$^2$ to 100 tons/in$^2$, 50 tons/in$^2$ to 200 tons/in$^2$, or 1 ton/in$^2$ to 200 tons/in 2. The disclosure provides a method wherein the hydraulic press applies compression of approximately 500 tons/in$^2$.

Example 6. Melanin and Iron Filings

Commercial cuttlefish ink was dried in a 900 watt microwave oven so that the product was 30% or 35% of the initial weight. A blender was used to mix and grind the melanin. A variety of formulations were made. In one formulation, the 30% preparation was mixed with 7% iron filings, and then the blender was used to mix again. In another formulation, 35% slabs were alternated with 30% slabs to create a layered composite. Each formulation was subjected to compression in a 20 ton/sq. in. hydraulic press for about 20 minutes. Because the platen was approximately 3.5 in. square, it is estimated that a force of approximately 3265 pounds/sq. in. was exerted on each sample formulation.

Example 7. Use of Formulations of Melanin Produced by Microwaving and Hydraulic Press Compression to Reduce Penetration of Bullets and Other Projectiles The melanin produced by the new method proved effective in reducing the penetration of a bullet.

Two slabs of melanin were produced by the method of example A. Each was approximately 3.5 in square. One slab was 1 inch thick and 1 slab was 0.5 in. thick. Both slabs were placed together in a wood frame to create a 1.5 inch thick sample of melanin. Several blocks of ballistic clay, approximately 3.5 in. square were placed behind the melanin sample. A control was created separately where the melanin sample was replaced by a (dummy) ballistic clay block. 9 mm bullets were fired at approximately 1200 ft/sec.

In the experimental setup, the bullet penetrated the melanin and then went a depth of approximately 6 cm into the clay. In the control setup the bullet penetrated the initial (dummy) clay block, and then penetrated 12 cm into the clay. This demonstrated that the melanin formulation showed effectiveness in reducing the bullet's penetration compared to the clay control.

Example 8. The Use of Elemental Metals Mixed with Melanin to Create New Formulations of Melanin with Novel Properties It was discovered that mixing elemental iron with melanin in the form of dried cuttlefish ink resulted in unexpected hardness of the material while it remains somewhat flexible. Under scanning electron microscopy it was demonstrated that the new formulation of melanin had organized into stacks of lamellae, which appeared to be composed of melanosomes. This is an entirely novel finding since, although metal ions are known to bind to the melanin, it does not appear that anyone has experimented with or reported that elemental iron can bind. This new disclosure is that iron and other elemental metals including, for example, copper, zinc, cesium, radium, strontium, thorium, or uranium, can bind to melanin and organize it in novel ways which confer upon it new properties. For instance, the new properties conferred will include enhanced hardness, stiffness, impact resistance, electrical conductivity, capacitance, semiconductor properties, and enhanced ability to absorb radiation including x-ray and gamma ray.

Example 9. Melanin and Iron Filings

Cuttlefish ink was dried using a microwave oven to 40% of its original weight. Iron filings were added so that they comprised 0.5% of the final formulation. The material felt harder than a similar sample without the 0.5% iron filings. Scanning electron microscopy revealed multiple areas where sharply defined lamellae with 900 corner angles were seen in stacks.

Example 10. A Practical Method for Formulating Melanin to be Placed into Pharmaceutical or Dietary Supplement Capsules, and Other Containers A novel method was developed to enable formulation of melanin (e.g. from cephalopod ink) into capsules or other containers for pharmaceutical, dietary supplement, and other uses.

Cuttlefish ink was dried using a microwave oven to 40% of its original weight. Cab-O-Sil, a pharmaceutical preparation of the excipient micronized silicon dioxide, was mixed to comprise 40% of the final mixture with the 40% dried cuttlefish ink. This mixture was placed in a hard size zero pharmaceutical capsule. It was noticed after seven days that the capsule became weak and flaccid and would be unsuitable for use. It was discovered that when the mixture of silicon dioxide and cuttlefish ink was dried for several days in a conventional oven at 40° C., then placed in the capsule and observed, the capsule remained intact and is suitable for human and animal use.

Example 11. Testing Melanin Blocks as Ballistic Armor

An experiment was conducted which tested the ability of melanin blocks to protect as armor against ammunition. Melanin blocks were constructed using procedures described herein. Cuttlefish ink was dehydrated to about 32% of its initial weight using a microwave oven and then put in a blender to reduce the size of its component particles. It was then compressed in a hydraulic press to blocks about 3.75 inches square and of 1-1.75 inch depth. Blocks of similar size composed of ballistic clay, e.g. Roma Plastilina #1, were constructed to use as a control. A wooden frame was made to hold the blocks. For the experimental setup, three melanin blocks were put one after the other in the frame. The first block, closest to the gun, was about 3.75 inches×3.75 inches×1.75 inches. For the control setup, three clay blocks of similar size were put one after the other in a similar frame. For testing, 9 mm bullets were fired from a Berettta M9 handgun.

In the case of the clay control setup, the bullet completely penetrated the first two clay blocks, and lodged in the third block. Parts of the first clay block were blown away, and the second and third clay blocks were knocked onto the floor. In the experimental setup, the bullet lodged in the first melanin block and never penetrated through it. When the bullet was taken by hand out of the block, it was discovered that it had penetrated into about the first 1.25 inches of the melanin block, but did not penetrate the last about 0.5 inches. The bullet itself was crushed and deformed. It was obvious that the first melanin block had successfully absorbed the bullet, crushed the bullet, and the bullet remained lodged in the block.

It was concluded that a single melanin block, formulated as described above and about 1.75 inches in depth, had absorbed and stopped a 9 mm bullet fired from a distance of 10 feet.

While the disclosure has been described in detail and with reference to specific examples thereof, it will be apparent to one skilled in the art that various changes and modifications can be made therein without departing from the spirit and scope thereof.

What is claimed is:

1. A ballistic protection material formed using a composition comprising:
    melanin material which has been dried in a microwave to form dried melanin material, and polyvinyl alcohol, methylparaben and propylparaben;
    mixing the dried melanin material and polyvinyl alcohol at a ratio of about 40 to about 60 to about 50 to about 50 (percent by weight) to form a mixture;
    compressing the mixture, wherein the compression is applied in a hydraulic press wherein the hydraulic press ranges in capacity from approximately 1 ton/in$^2$ to approximately 50 tons/in$^2$,
    thereby forming the ballistic protection material, wherein the ballistic protection material is manufactured in a form selected from the group consisting of slabs, plates, and bricks.

2. The ballistic protection material of claim 1, wherein the ballistic protection material is formed into an article which is an item selected from the group consisting of helmets, body armor, vehicle armor, aircraft armor, watercraft armor, structure armor, equipment housing, blast protection panels, ballistic protection panels, and cargo containers.

3. A process for forming a ballistic protection material, comprising the steps of:
    drying melanin material in a microwave to produce dried melanin material;
    providing polyvinyl alcohol, methylparaben, and propylparaben;
    mixing the dried melanin material with polyvinyl alcohol in a ratio of about 40:60 to about 50:50 by weight to form a mixture, and adding methylparaben and propylparaben to the mixture;
    compressing the mixture using a hydraulic press with a capacity ranging from approximately 1 ton/in$^2$ to approximately 50 tons/in$^2$, thereby forming a ballistic protection material, wherein the material is manufactured in a form selected from the group consisting of slabs, plates, and bricks.

4. The process of claim 3, further comprising a step of shaping which comprises using a technique selected from the group consisting of molding, compression molding, stamping, bending, thermoforming, injection molding, additive manufacturing, coining, and extruding.

5. The process of claim 3, wherein the melanin material and the non-melanin material are mixed using a machine selected from the group consisting of a single screw extruder, a counter-rotating twin-screw extruder, a co-rotating twin-screw extruder, a Henschel mixer, and a co-kneader.

6. The process of claim 3, wherein the ballistic protection material is formed into an article which is an item selected from the group consisting of helmets, body armor, vehicle armor, aircraft armor, watercraft armor, structure armor, equipment housing, blast protection panels, ballistic protection panels, and cargo containers.

* * * * *